United States Patent [19]

Dutta et al.

[11] 4,100,274
[45] Jul. 11, 1978

[54] POLYPEPTIDE

[75] Inventors: Anand Swaroop Dutta; Barrington John Albert Furr; Michael Brian Giles, all of Macclesfield, England

[73] Assignee: Imperial Chemical Industries Limited, London, England

[21] Appl. No.: 790,003

[22] Filed: Apr. 22, 1977

[30] Foreign Application Priority Data

May 11, 1976 [GB] United Kingdom ............... 19327/76

[51] Int. Cl.$^2$ .................... A61K 37/00; C07C 103/52
[52] U.S. Cl. ........................... 424/177; 260/112.5 LH
[58] Field of Search ............... 260/112.5 LH; 424/177

[56] References Cited

U.S. PATENT DOCUMENTS

| | | | |
|---|---|---|---|
| 3,896,104 | 7/1975 | McKinley et al. | 260/112.5 LH |
| 3,901,872 | 8/1976 | McKinley et al. | 260/112.5 LH |
| 3,914,412 | 10/1975 | Cendrich et al. | 260/112.5 LH |
| 3,971,737 | 7/1976 | Garsky | 260/112.5 LH |
| 3,992,530 | 11/1976 | Foell et al. | 260/112.5 LH |
| 4,005,063 | 1/1977 | Gendrich et al. | 260/112.5 LH |
| 4,010,125 | 3/1977 | Schally et al. | 260/112.5 LH |
| 4,010,149 | 3/1977 | Baka et al. | 260/112.5 LH |
| 4,018,726 | 4/1977 | Schally et al. | 260/112.5 LH |
| 4,024,121 | 5/1977 | Schally et al. | 260/112.5 LH |
| 4,024,248 | 5/1977 | Konig et al. | 260/112.5 LH |

*Primary Examiner*—Delbert R. Phillips
*Attorney, Agent, or Firm*—Cushman, Darby & Cushman

[57] ABSTRACT

The disclosure relates to novel luliberin analogues which possess luliberin agonist activity, to processes for their manufacture and to compositions containing them. Typical of the peptides disclosed is

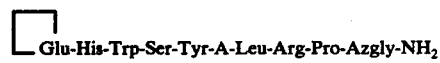
Glu-His-Trp-Ser-Tyr-A-Leu-Arg-Pro-Azgly-NH$_2$ in which A is D-Phe, D-Tyr(Me) or D-Ser(Bu$^t$).

6 Claims, No Drawings

POLYPEPTIDE

This invention relates to a polypeptide which possesses luliberin agonist properties, luliberin being the internationally-approved trivial name for LH-RF (luteinising hormone releasing factor) (J. Biol. Chem., 1975, 250, 3215)

It is known (Dutta, Furr, Giles and Morley, Clinical Endocrinology, 1976, 5, Supplement, p. 291s–298s) that substitution of α-aza-amino-acids at positions 6 or 10 of luliberin produces compounds which are less potent than the parent molecule in their ability to release luteinising hormone (LH) from the pituitary gland. It has now been found that substitution of azaglycine at position 10 combined with the substitution of various D-α-amino-acids at position 6 in luliberin or substitution of azaglycine or azalanine at position 6 combined with replacement of the terminal glycine amide by an ethylamino radical in luliberin produces compounds which are more active than luliberin in their ability to release luteinising hormone.

According to the invention there is provided a polypeptide of the formula:

Glu-His-Trp-Ser-Tyr-A-B-Arg-Pro-E-F

I in which A is D-Tyr, D-Tyr(Me), D-Ser, D-Ser(Bu$^t$), D-Phe, D-Ala or D-Trp, B is Leu or MeLeu, E is Azgly and F is an amino radical, or A is Azgly or Azala, B is Leu, E is a direct bond and F is an ethylamino radical; and the pharmaceutically- and veterinarily-acceptable acid-addition salts thereof.

In the above formula I and throughout this specification, the amino-acid residues are designated by their standard abbreviations (Pure and Applied Chemistry, 1974, 40, 317–331). An α-aza-amino-acid residue is one in which the α-CH of an amino-acid has been replaced by nitrogen. The abbreviation for an α-aza-amino-acid is derived from that of the corresponding amino-acid by inserting the "Az" prefix. Thus Azgly stands for azaglycine and Azala stands for azalanine. Where the configuration of a particular amino-acid is not designated, that amino-acid (apart from the α-aza-amino-acids which contain no asymmetric centre adjacent to the carboxy group) has the natural L-configuration.

Particular groups of compounds within the compounds of the invention are as follows:

Those wherein A is D-Tyr, D-Tyr(Me), D-Ser, D-Ser(Bu$^t$), D-Phe, D-Ala or D-Trp, B is Leu or MeLeu, E is Azgly and F is an amino radical.

Those wherein A is Azgly or Azala, B is Leu, E is a direct bond and F is an ethylamino radical.

Those wherein A is D-Tyr(Me), D-Ser, D-Ser(Bu$^t$), D-Phe, D-Ala or D-Trp, B is Leu or MeLeu, E is Azgly and F is an amino radical.

A preferred group of compounds of the invention is that wherein A is D-Tyr(Me), D-Ser(Bu$^t$) or D-Phe, B is Leu or MeLeu, E is Azgly and F is an amino radical.

The three preferred compounds of the invention have the following structures:

Glu-His-Trp-Ser-Tyr-D-Phe-Leu-Arg-Pro-Azgly-NH$_2$

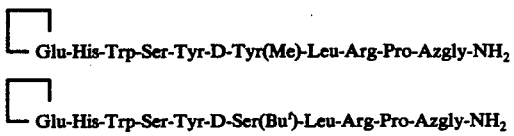
Glu-His-Trp-Ser-Tyr-D-Tyr(Me)-Leu-Arg-Pro-Azgly-NH$_2$

Glu-His-Trp-Ser-Tyr-D-Ser(Bu$^t$)-Leu-Arg-Pro-Azgly-NH$_2$

A particular pharmaceutically- or veterinarily-acceptable acid-addition salt of the invention is, for example, a hydrochloride, phosphate, citrate or acetate.

The polypeptide of the invention may be manufactured by methods known in themselves for the manufacture of chemically-analogous compounds. Thus the following processes, A, B, E and F having the meanings stated above, are provided as further features of the invention:

(a) removal of one or more conventional peptide protecting groups from a protected polypeptide to give the compound of the formula I;

(b) reaction of

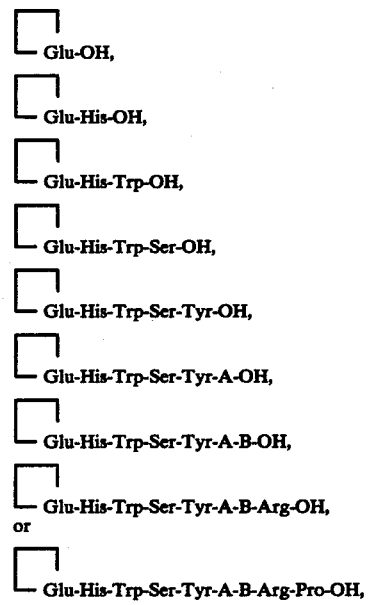

Glu-OH,

Glu-His-OH,

Glu-His-Trp-OH,

Glu-His-Trp-Ser-OH,

Glu-His-Trp-Ser-Tyr-OH,

Glu-His-Trp-Ser-Tyr-A-OH,

Glu-His-Trp-Ser-Tyr-A-B-OH,

Glu-His-Trp-Ser-Tyr-A-B-Arg-OH, or

Glu-His-Trp-Ser-Tyr-A-B-Arg-Pro-OH, or a suitable activated derivative of any of these, with H-His-Trp-Ser-Tyr-A-B-Arg-Pro-E-F, H-Trp-Ser-Tyr-A-B-Arg-Pro-E-F, H-Ser-Tyr-A-B-Arg-Pro-E-F, H-Tyr-A-B-Arg-Pro-E-F, H-A-B-Arg-Pro-E-F, H-B-Arg-Pro-E-F, H-Arg-Pro-E-F, H-Pro-E-F or H-Azgly-NH$_2$ respectively, or a suitable activated derivative of any of these, in a standard peptide coupling reaction; or (c) reaction of a carboxylic acid of the formula

Glu-His-Trp-Ser-Tyr-A-B-Arg-Pro-E-OH,

II or an activated derivative thereof with ammonia or ethylamine.

In process (a) there may be as many protecting groups in the starting material as there are radicals which may require protection, for example some or all of those radicals which exist in the product as free OH radicals or basic NH radicals.

In process (a) the protecting group or groups may be those described in a standard text book on peptide chemistry, for example M. Bodansky and M. A. Ondetti, "Peptide Synthesis", Interscience, New York, 1966, Chapter IV; F. M. Finn and K. Hofmann, "The Proteins", Vol. II, edited by H. Neurath and R. L. Hill, Academic Press Inc., New York, 1976, p.106; "Aminoacids, Peptides and Proteins" (Specialist Periodical Reports), The Chemical Society, London, volumes 1 to 8. Various methods for the removal of the protecting groups are also described in these books.

In process (a) a particularly useful NH protecting group is the benzyloxycarbonyl radical and a particularly useful OH protecting group is the benzyl radical. Both these groups may be readily removed by hydrogenolysis, for example in the presence of a palladium-on-charcoal catalyst.

In process (a) a further particularly useful NH protecting group is the t-butoxycarbonyl radical and a further particularly useful OH protecting group is the t-butyl radical. Both these groups may be readily removed by treatment with an acid such as hydrogen chloride or trifluoroacetic acid.

In process (a) a further particularly useful NH protecting group is the benzyloxycarbonyl or t-butoxycarbonyl radical and a particularly useful OH protecting group is the t-butyl radical. These protecting groups may be readily removed by treatment with HBr in acetic acid.

In process (b) any one of the standard peptide coupling reactions may be used, for example those described in a standard text book on peptide chemistry, for example the above text book by Bodansky and Ondetti, Chapter V, and the above volumes 1 to 8 of Specialist Periodical Reports of the Chemical Society.

In process (b) a particular coupling reaction is an azide coupling, an active ester coupling or a coupling involving N,N'-dicyclohexylcarbodi-imide and 1-hydroxybenzotriazole. A preferred coupling reaction is an azide coupling, and in particular such a coupling which forms the His-Trp or Ser-Tyr peptide bond.

In process (c) a suitable activated derivative of the starting material is, for example, an ester or anhydride. In the case of an activated derivative the reaction may be conducted by bringing the activated derivative into contact with ammonia or ethylamine in the presence of a diluent or solvent. In those cases in which the starting material is the free acid of the formula II, the reaction with ammonia or ethylamine is conveniently brought about by a standard peptide coupling reagent such as N,N'-dicyclohexylcarbodi-imide.

The starting materials for use in the processes of the invention may be prepared, from known compounds, by standard peptide coupling reactions, standard peptide protection reactions and standard peptide deprotection reactions well known to one skilled in this art, for example as set out in Examples 1 to 10.

As noted above the compound of the invention has luliberin agonist properties, that is it mimics the actions of luliberin, a natural hormone secreted by the hypothalamus which acts on the pituitary gland causing it to release luteinising hormone (LH) and follicle stimulating hormone (FSH). These two pituitary hormones are involved in controlling reproductive processes, the latter, FSH, acting on the ovaries to promote maturation of follicles and the former, LH, to induce ovulation. The compound of the formula I is unexpectedly more potent than luliberin in its ability to release LH, and is therefore useful in controlling and/or improving reproduction in animals. It is, in particular, useful in the breeding of large domestic animals during anoestrus and in any artificial breeding situation to control the time of ovulation more precisely. It may also be useful in ameliorating infertility states in men and women.

The luliberin agonist effect of the compound of the invention may be demonstrated, for example, by its ability to induce ovulation in androgen-sterilised constant oestrus rats, or by its ability to release LH and FSH, as measured by double antibody radioimmunoassay, into the blood plasma of immature male rats or into the blood plasma of anoestrus or dioestrus ewes.

The above test on androgen-sterilised rats is carried out as follows:

Androgen-sterilised female rats prepared by treating rats at days 3, 4 and 5 of age with 100 $\mu$g testosterone propionate having a persistent oestrus vaginal smear and numerous preovulatory follicles in the ovaries. Administration of luliberin and active analogues causes the release of an ovulatory surge of LH and FSH which can be assessed by the presence of ova in the Fallopian tubes and fresh corpora lutea in the ovaries.

All the compounds exemplified in this specification are more active than luliberin in their ability to induce ovulation in constant oestrus rats and in addition show no toxic effects when dosed at at least four times their minimum active dose. In particular the preferred compounds of the invention, those described in Examples 4, 6 and 7, are approximately one hundred times as active as luliberin and they display no toxic effects when dosed at one hundred times their minimum effective dose.

According to a further feature of the invention there is provided a pharmaceutical or veterinary composition which comprises as active ingredient the compound of the invention in association with a pharmaceutically- or veterinarily-acceptable diluent or carrier.

The composition of the invention may, for example, be in a form suitable for oral or buccal administration, for example a tablet, capsule, solution or suspension; nasal administration, for example a snuff, nasal spray or nasal drops; vaginal or rectal administration, for example a suppository; or parenteral administration, for example a sterile injectable solution or suspension.

In general, the above compositions may be prepared in a conventional manner using conventional excipients. However, in the case of a composition for oral administration, it may be convenient for the composition to include a coating to protect the polypeptide active ingredient from the actions of enzymes in the stomach.

The composition of the invention may also contain, in addition to the polypeptide of the invention, one or more known drugs selected from a prostaglandin derivative such as prostaglandin $F_2\alpha$, cloprostenol or fluprostenol or another drug such as clomiphene or tamoxifen.

A preferred composition of the invention is one suitable for oral administration in unit dosage form for example a tablet, capsule, drench or bolus which contains from 2.5 to 500 mg., and preferably 10 to 100 mg., of polypeptide in each unit dose, or one suitable for parenteral administration which contains from 5 $\mu$g. to 1 mg. of polypeptide per ml., and preferably 10 $\mu$g. to 100 $\mu$g. of polypeptide per ml. of solution.

A parenteral composition is preferably a solution in isotonic saline or isotonic dextrose, buffered if necessary to a pH of 5 to 9. Alternatively, the parenteral composition may be one designed for slow release in which case the amount of polypeptide per unit dose is in general greater than that required when a conventional injectable formulation is used. A preferred slow release parenteral formulation contains from 100 μg. to 1.0 mg. of polypeptide per unit dose.

The composition of the invention will normally be administered such that a daily oral dose will be from 50 μg./kg., to 20 mg./kg., and a daily parenteral dose, for example by intravenous, subcutaneous or intramuscular injection or infusion, will be from 0.2 μg./kg. to 100 μg./kg. In humans these doses are equivalent to a total daily dose of 3.5 mg. to 1.4 g. administered orally and a total daily dose of 14 μg. to 7 mg. administered parenterally. When administered via the mucous membranes, the dose ranges will be intermediate between the oral and parenteral ranges given above.

The invention is illustrated, but not limited, by the following Examples:

In the Examples, $R_f$ refers to ascending thin layer chromatography (t.l.c.) on silica gel plates (Kieselgel G). The solvent systems used in this chromatography were butan-1-ol/acetic acid/water (4:1:5 v/v) ($R_fA$), butan-1-ol/acetic acid/water/pyridine (15:3:12:10 v/v) ($R_fB$), butan-2-ol/3% w/v aqueous ammonium hydroxide (3:1 v/v) ($R_fC$), acetonitrile/water (3:1 v/v) ($R_fD$), acetone/chloroform (1:1 v/v) ($R_fE$), chloroform/ethanol (1:4 v/v) ($R_fF$), cyclohexane/ethyl acetate (1:1 v/v) ($R_fG$), cyclohexane/ethyl acetate/methanol (1:1:1 v/v) ($R_fH$), chloroform/methanol/water (11:8:2 v/v) ($R_fK$), chloroform/methanol (19:1 v/v) ($R_fP$) and chloroform/methanol (9:1 v/v) ($R_fQ$). In all cases, plates were examined under U.V. light and treated with fluorescamine, ninhydrin, and chlorine-starch-iodide reagents. Unless otherwise stated, the quoting of an $R_f$ implies that a single spot was revealed by these methods.

Acid hydrolysates of all products described in this specification were prepared by heating the peptide or protected peptide with 6N-hydrochloric acid containing 1% w/v phenol in a sealed evacuated tube for 16 hours at 100° C. The amino-acid composition of each hydrolysate was determined with a LoCarte Amino-acid Analyser, and in each case was in agreement with the expected composition. The term "worked up in the usual manner" used in the Examples implies that after the reaction any solid residue was removed by filtration, the filtrate evaporated to dryness below 40° C., the residue in ethyl acetate was washed with a 20% citric acid solution, water, saturated sodium hydrogen carbonate solution and water, dried over anhydrous sodium sulphate and the ethyl acetate was evaporated in vacuo to leave the compound.

EXAMPLES 1 TO 10

Synthesis of
L-pyroglutamyl-L-histidyl-L-tryptophyl-L-seryl-L-tyrosyl-A-L-leucyl-L-arginyl-L-prolyl-E-F. General process (m) (Schemes 1 and 2)

To a cooled (0° C.) and stirred suspension of L-pyroglutamyl-L-histidine hydrazide (0.2 mmole) in dimethylformamide (0.9 ml.) and dimethylsulphoxide (0.7 ml.) 5.7N hydrogen chloride in dioxan (0.8 mmole) was added. A clear solution was obtained after 5 minutes vigorous stirring. The solution was cooled to −20° C., t-butylnitrite (0.22 mmole) was added and the stirring was continued for 25 minutes. The temperature was then lowered to −30° C. and the solution was neutralised by adding triethylamine (0.8 mmole). A precooled (−20° C.) mixture of L-tryptophyl-L-seryl-L-tryrosyl-A-L-leucyl-L-arginyl-L-prolyl-E-F dihydrochloride (0.1 mmole, obtained by the hydrogenolysis of the N-benzyloxycarbonyl derivative in 80% v/v aqueous methanol containing two equivalents of hydrogen chloride over 5% w/w palladium-on-charcoal for 16 hours) and triethylamine (0.1 mmole) in dimethylformamide (1 ml.) was added and the reaction mixture was stirred for 24 hours at 4° C. Dimethylformamide was evaporated in vacuo and the residue was chromatographed on Sephadex LH-20 using dimethylformamide as eluant. The peptide hydrochloride was further purified by partition chromatography on Sephadex G-25 using the solvent system n-butanol/acetic acid/water/pyridine (5:1:5:1 v/v).

Synthesis of
L-pyroglutamyl-L-histidyl-L-tryptophyl-L-seryl-L-tyrosyl-A-B-L-arginyl-L-prolyl-azaglycine amide.
General process (n) (Schemes 3, 4 and 5)

L-Pyroglutamyl-L-histidyl-L-tryptophyl-L-serine hydrazide (0.2 mmole) was dissolved in dimethylformamide (4 ml.) and was converted to the azide as described in process (m). It was coupled, as described in process (m), with L-tyrosyl-A-B-L-arginyl-L-prolyl-azaglycine amide hydrochloride (0.15 mmole), prepared by the catalytic reduction of N-benzyloxycarbonyl-O-benzyl-L-tyrosyl-A-L-leucyl-(N$^\omega$-nitro)-L-arginyl-L-prolyl-azaglycine amide in 80% v/v aqueous methanol for 20 hours over 5% w/w palladium-on-charcoal, and the final product as the hydrochloride was purified as above.

Synthesis of
L-pyroglutamyl-L-histidyl-L-tryptophyl-L-seryl-L-tyrosyl-A-B-L-arginyl-L-prolyl-azaglycine amide.
General process (o) (Schemes 4 and 6)

A solution of the protected decapeptide derivative (having Ser(Bu$^t$) in position 6 or Tyr(Bu$^t$) in position 5) (50 mg.) was dissolved in 90% v/v aqueous trifluoroacetic acid (5 ml.). Three drops of β-mercaptoethanol were added and the solution was left at room temperature for 45 minutes. The solvent was removed in vacuo and the residue was freeze-dried once from water and twice from t-butanol. Yield 90–100%.

The compounds of the invention prepared by one of these three general procedures are listed in Examples 1 to 10 in the following Table:

TABLE

Glo-His-Trp-Ser-Tyr-A-B-Arg-Pro-E-F-

| Ex. No. | A | B | E | F | Process | Yield % | Paper electrophoresis $R_P$ (relative to luliberin) | | $R_fA$ |
| --- | --- | --- | --- | --- | --- | --- | --- | --- | --- |
| | | | | | | | pH 2.1 | pH 6.5 | |
| 1 | Azgly | Leu | — | —NHC$_2$H$_5$ | m | 25 | 0.98 | 1.03 | 0.28 |

TABLE-continued

Glo-His-Trp-Ser-Tyr-A-B-Arg-Pro-E-F-

| Ex. No. | A | B | E | F | Process | Yield % | Paper electrophoresis $R_F$(relative to luliberin) pH 2.1 | pH 6.5 | $R_fA$ |
|---|---|---|---|---|---|---|---|---|---|
| 2 | Azala | Leu | — | —NHC$_2$H$_5$ | m | 42 | 0.97 | 1.0 | 0.30 |
| 3 | D-Ala | Leu | Azgly | NH$_2$ | m | 32 | 0.97 | 1.0 | 0.30 |
| 4 | D-Phe | Leu | Azgly | NH$_2$ | n | 40 | 1.0 | 0.71 | 0.27 |
| 5 | D-Trp | Leu | Azgly | NH$_2$ | n | 15 | 0.53 | 0.37 | 0.37 |
| 6 | D-Tyr(Me) | Leu | Azgly | NH$_2$ | n | 15 | 0.92 | 0.87 | 0.25 |
| 7 | D-Ser(Bu$^t$) | Leu | Azgly | NH$_2$ | n | 31 | 0.94 | 0.96 | 0.25 |
| 8 | D-Ser | Leu | Azgly | NH$_2$ | o | 95 | 0.94 | 0.96 | 0.25 |
| 9 | D-Phe | MeLeu | Azgly | NH$_2$ | o | 46 | 0.84 | 0.87 | 0.35 |
| 10 | D-Tyr(Me) | MeLeu | Azgly | NH$_2$ | n | 26 | 0.87 | 0.90 | 0.34 |

The starting materials for use in the above processes may be obtained as set out in the following schemes 1 and 2 (process (m)), schemes 3, 4 and 5 (process (n)) and schemes 4 and 6 (process (o)).

In these schemes the following contractions are used:
OCp = 2,4,5-trichlorophenyl ester
Bzl = benzyl
Z = benzyloxycarbonyl
Boc = t-butoxycarbonyl
DMF = dimethylformamide The circled numbers refer to the particular step involved.

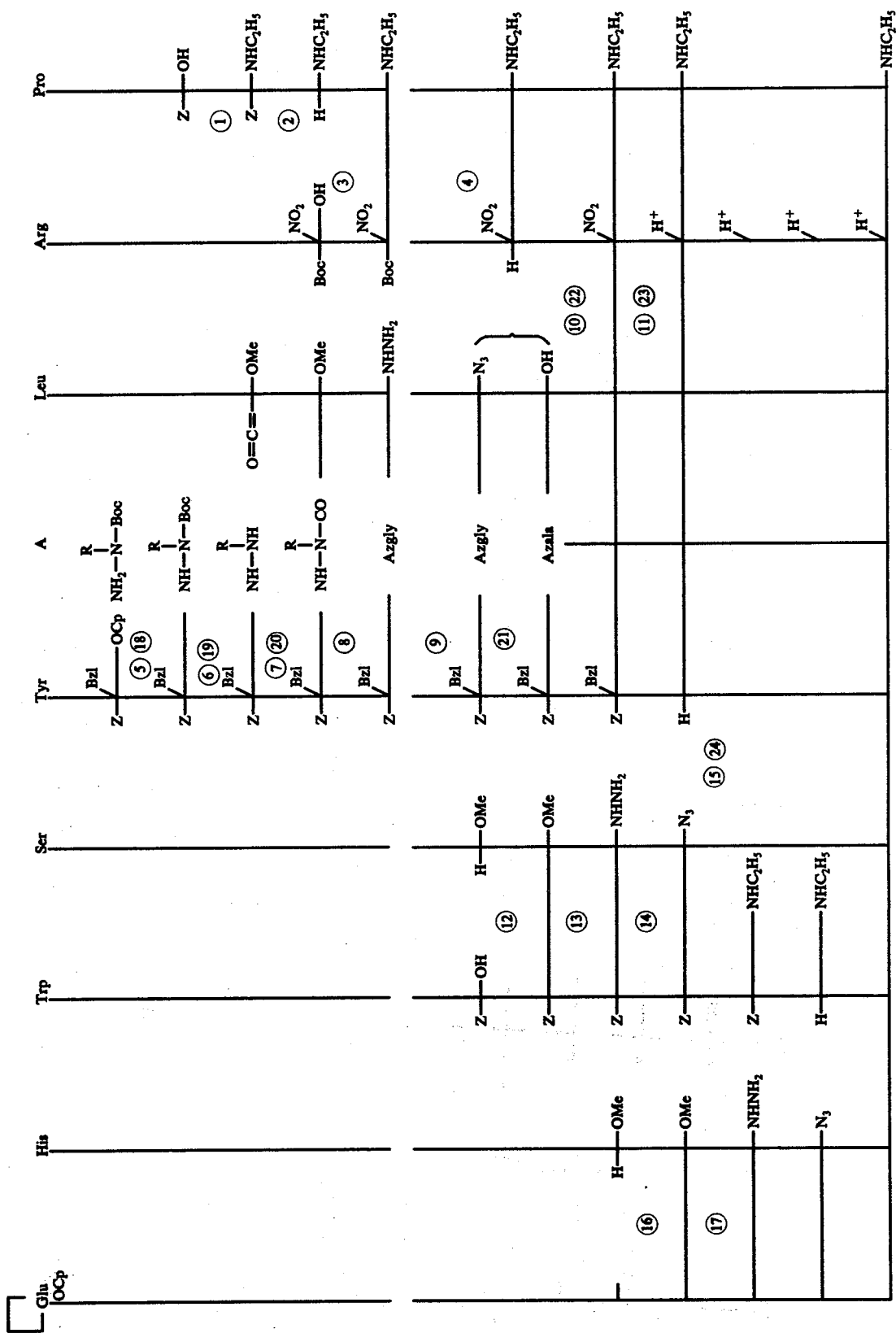

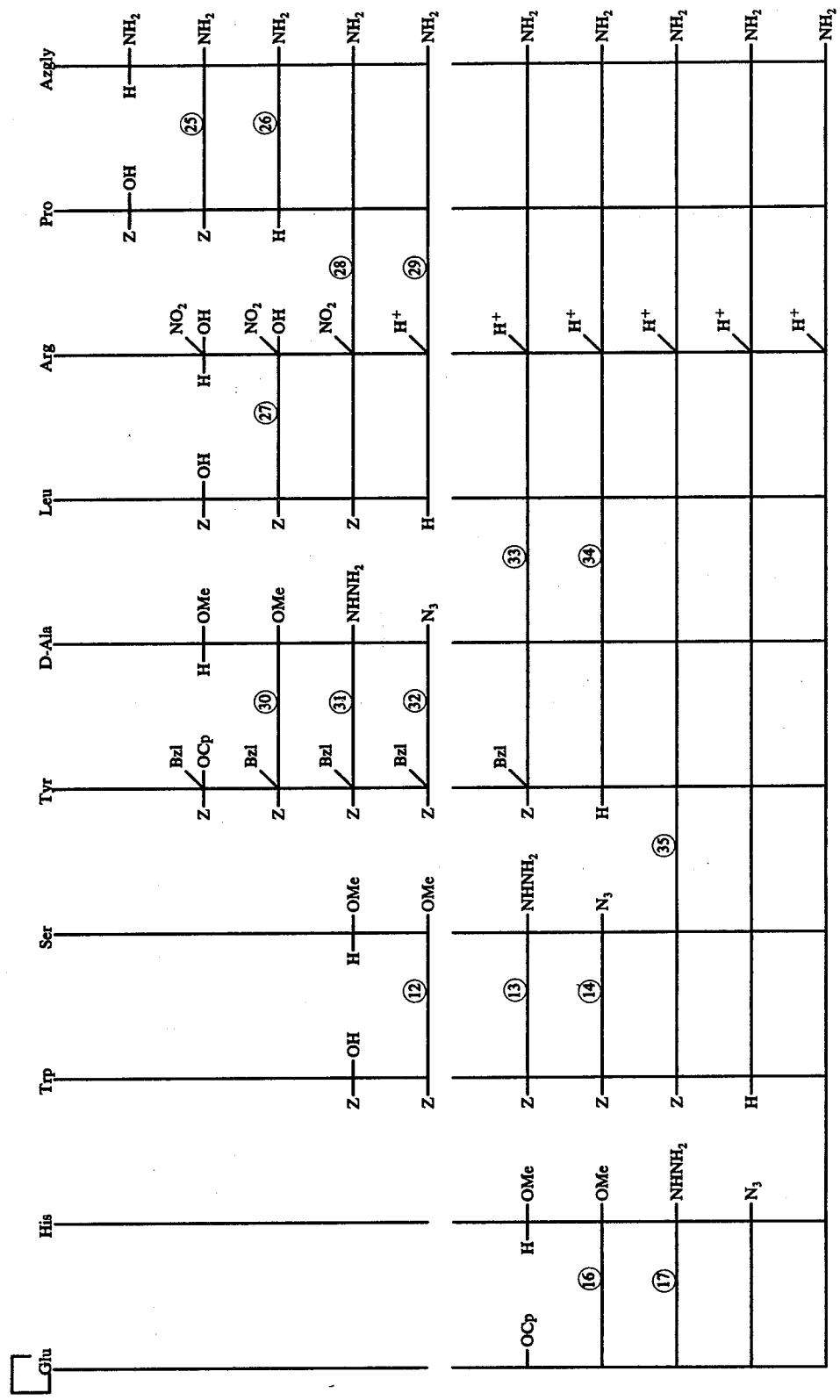
Scheme 2

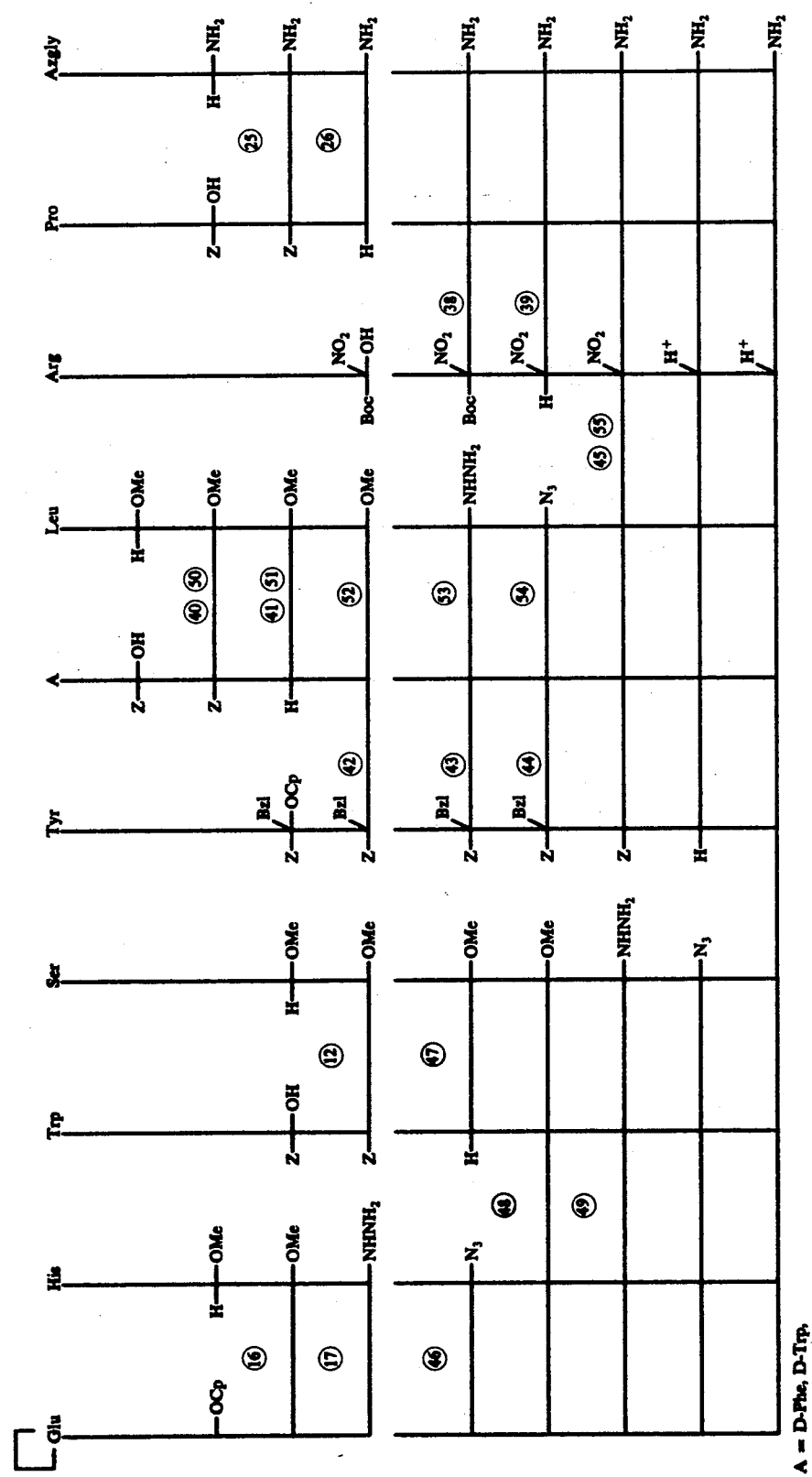

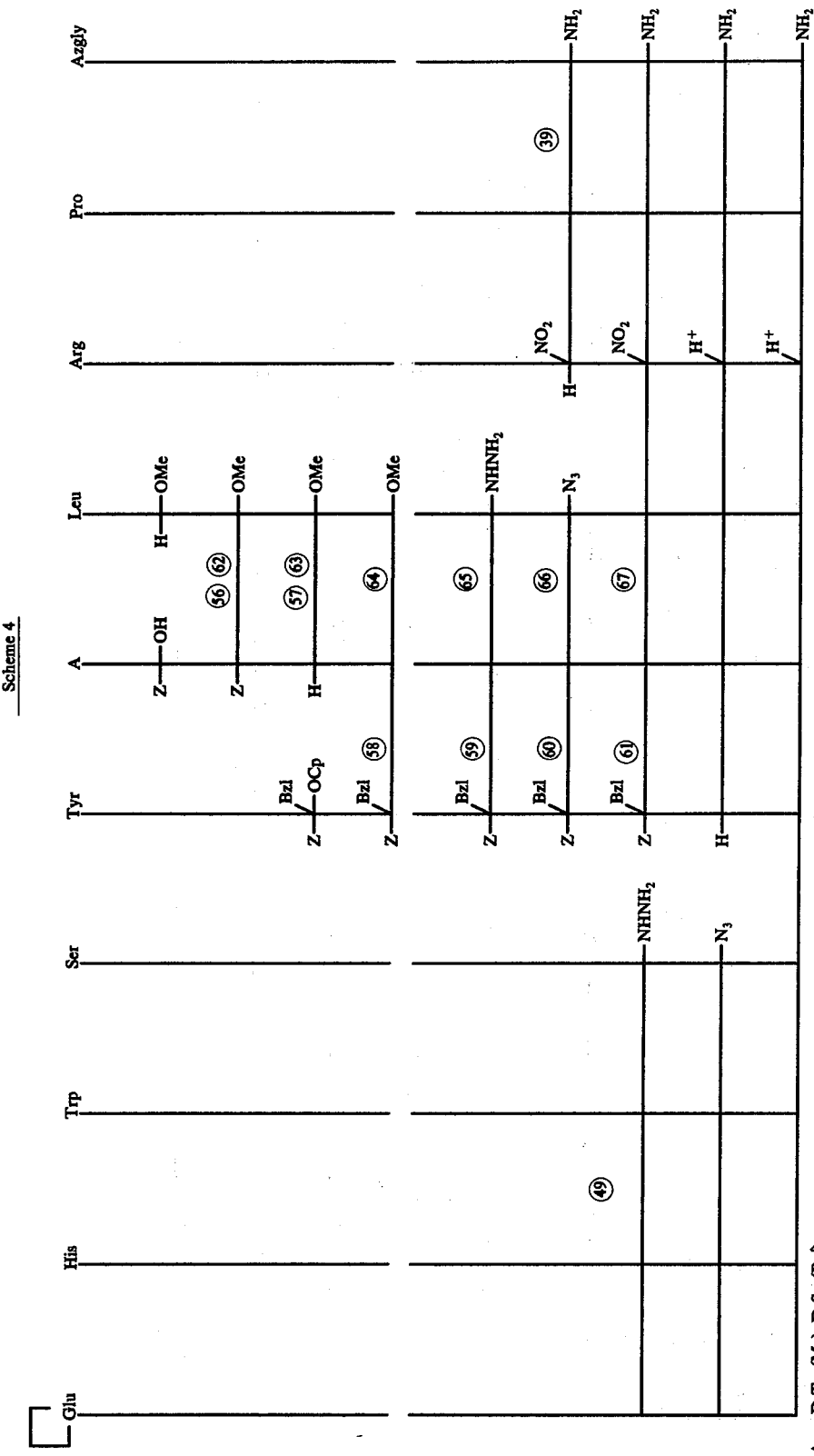

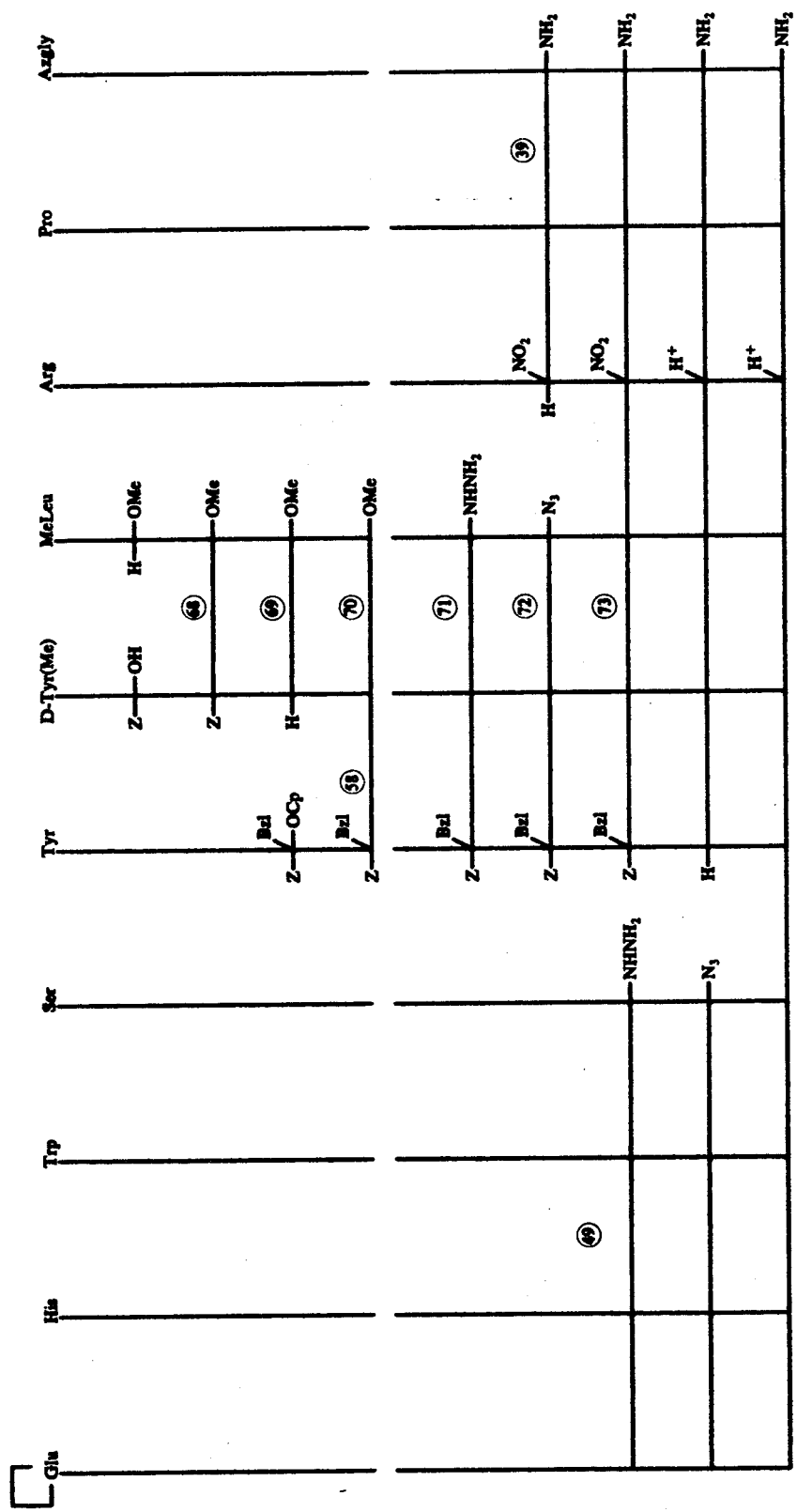

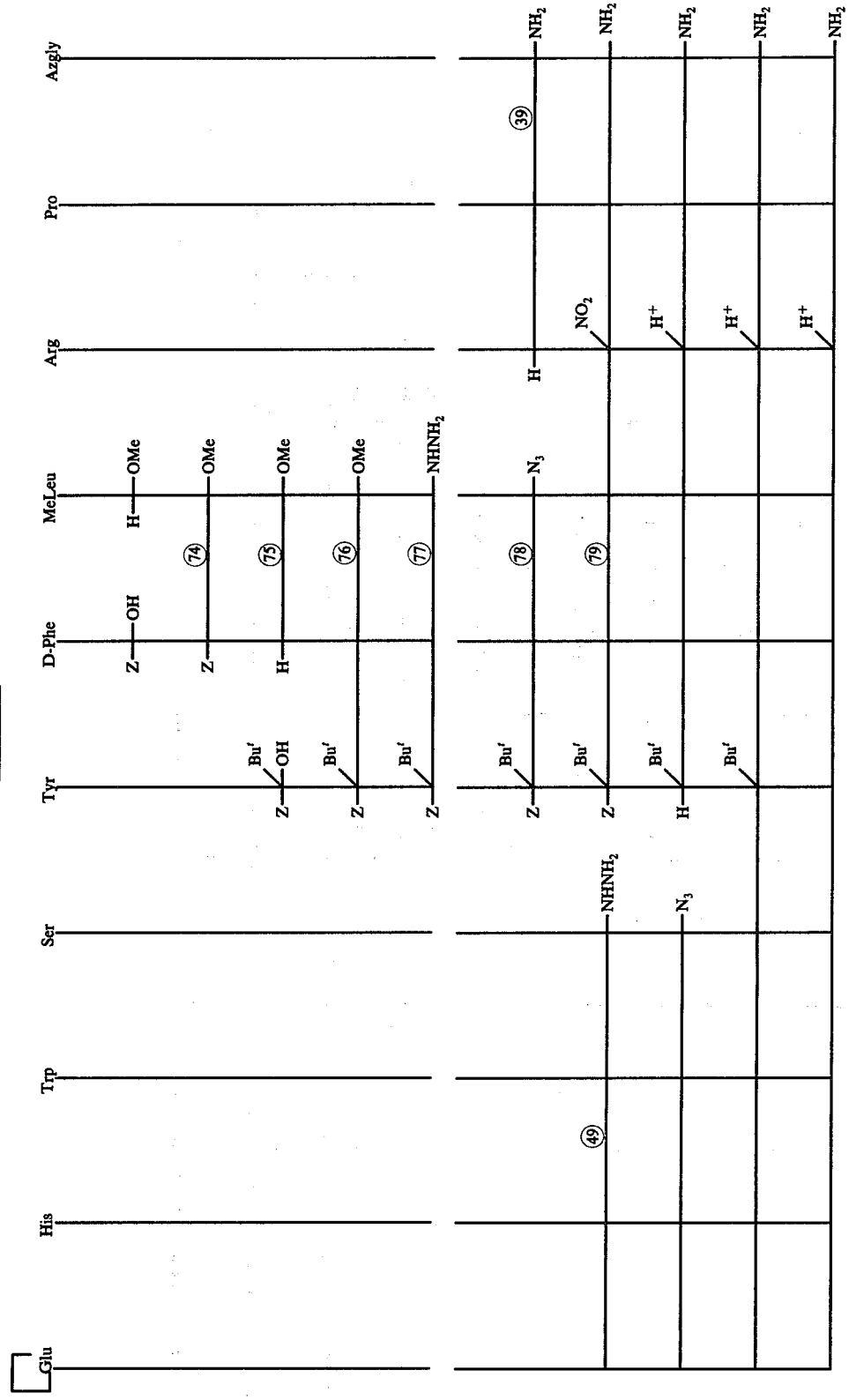

Step ①. N-Benzyloxycarbonyl-L-proline (19.94 g., 80 mmole) and N-methylmorpholine (8.8 ml., 80 mmole) were dissolved in dry tetrahydrofuran (200 ml.) and the solution was cooled to −20° C. Ethyl chloroformate (7.15 ml., 76 mmole) was added dropwise and after 2 minutes stirring a precooled (−20° C.) 70% aqueous solution of ethylamine (20 ml., 300 mmole) was added and the stirring was continued for 18 hours at 4° C. The reaction mixture was worked up in the usual manner and the residue was crystallised from ethyl acetate/petroleum ether (b.p. 60°–80° C.) Yield 12.97 g. (58.7%), m.p. 107°–108° C., $[\alpha]_D^{25.5}$ −43.88°(c, 1 in methanol), $R_fD$ 0.69, $R_fE$ 0.53, $R_fF$ 0.67, $R_fH$ 0.62, $R_fP$ 0.57, $R_fQ$ 0.66.

Step ②. Catalytic reduction over 5% Pd/C in aqueous ethanol containing one equivalent of hydrogen chloride for 5 hours at room temperature.

Step ③. A solution of $N^\alpha$-t-butoxycarbonyl-$N^\omega$-nitro-L-arginine (13.5 g., 42.3 mmole), L-proline ethyl amide hydrochloride (7.15 g., 47 mmole), 1-hydroxybenzotriazole (11.5 g., 85 mmole) and triethylamine (6.58 ml., 47 mmole) in DMF was cooled to 0° C. and dicyclohexylcarbodi-imide (9.13 g., 44.4 mmole) was added. The reaction mixture was stirred overnight at 4° C., filtered to remove the solid material, and the filtrate was evaporated to dryness in vacuo. The residue was partitioned between ethyl acetate and water by counter current distribution (4 transfers). The aqueous phases were combined, evaporated to dryness, and the residue was partitioned between n-butanol and 5% v/v aqueous acetic acid by counter current distribution (12 transfers). The crude peptide obtained by evaporating the combined n-butanol phases was purified by silica gel column chromatography using 5% v/v methanol in chloroform and 10% v/v methanol in chloroform as eluting solvents. The product containing fractions were combined, evaporated to dryness, and an aqueous solution of the residue was passed through an anion exchange resin (AG 1-X2) column to remove $N^\alpha$-t-butoxycarbonyl-$N^\omega$-nitro-arginine. The column was then washed with water, and the combined aqueous phases and the washings were freeze-dried to give the azapeptide derivative, yield 16.67 g. (89%), m.p. 109°–111° C. (decomp.), $[\alpha]_D^{25}$ −39.0° (c, 1 in methanol), $R_fA$ 0.62, $R_fB$ 0.74, $R_fC$ 0.59, $R_fD$ 0.70, $R_fE$ 0.20, $R_fF$ 0.60, $R_fH$ 0.61, $R_fK$ 0.85, $R_fQ$ 0.13.

Step ④. N-t-Butoxycarbonyl derivative was dissolved in ethyl acetate and treated with 3N HCl in ethyl acetate solution (4 equivalents) for 1 hour at room temperature.

Step ⑤ (R=H). A solution of t-butoxycarbonylhydrazide (2.90 g., 22 mmole) and N-benzyloxycarbonyl-O-benzyl-L-tyrosine 2,4,5-trichlorophenyl ester (11.71 g., 20 mmole) in dimethylformamide (40 ml.) was kept overnight at room temperature. Working up in the usual manner followed by recrystallisation of the residue from ether/petroleum ether (b.p. 60°–80° C.) yielded the protected hydrazide as a white powder, 3.46 g., (67%), m.p. 126°–127°, $[\alpha]_D^{25}$ −13.2°(c, 1 in methanol), $R_fD$ 0.82, $R_fE$ 0.65, $R_fF$ 0.63, $R_fH$ 0.70.

Step ⑥ (R=H). 1-(N-Benzyloxycarbonyl-O-benzyl-L-tyrosyl)-2-t-butoxycarbonyl hydrazide (5.19 g., 10 mmole) was dissolved in ethyl acetate (50 ml.) and was treated with 5N hydrogen chloride in ethyl acetate (8 ml., 40 mmole) for one hour at room temperature. Ethyl acetate was removed in vacuo and the hydrochloride was filtered with ether and dried.

Step ⑦ (R=H). The above hydrochloride was taken up in tetrahydrofuran (75 ml.) and triethylamine (1.15 g., 8 mmole) was added followed by N-carbonyl-L-leucine methyl ester (1.36 g., 8 mmole). After 16 hours at room temperature the reaction mixture was worked up in the usual manner and the residue was recrystallised from ethyl acetate/petroleum ether (b.p. 60°–80° C.) to give the azatripeptide derivative, 4.57 g. (77.7%), m.p. 156°–157° C., $[\alpha]_D^{24}$ −10.3° (c, 1 in methanol), $R_fD$ 0.81, $R_fE$ 0.45, $R_fP$ 0.26, $R_fQ$ 0.47.

Step ⑧. Hydrazine hydrate (5 ml., 100 mmole) was added to a solution of N-benzyloxycarbonyl-O-benzyl-L-tyrosylazaglycyl-L-leucine methyl ester (2.95 g., 5 mmole) in methanol (50 ml.). After 2 hours at room temperature the hydrazide was precipitated with water and recrystallised from methanol/ether, yield 2.74 g. (92.8%), m.p. 169°–170° C., $[\alpha]_D^{24}$ −9.05°(c, 1 in dimethylformamide), $R_fA$ 0.76, $R_fB$ 0.75, $R_fC$ 0.73, $R_fD$ 0.63, $R_fF$ 0.60, $R_fH$ 0.55.

Steps ⑨ and ⑩ (R=H). N-Benzyloxycarbonyl-O-benzyl-L-tyrosylazaglycly-L-leucine hydrazide (1.18 g., 2.0 mmole) was dissolved in dimethylformamide (10 ml.) and after cooling the solution to −20° C. a 5.49M solution of hydrogen chloride in dioxan (1.46 ml., 8 mmole) was added followed by t-butyl nitrite (0.25 ml., 2.2 mmole). After 5 minutes the solution was cooled to −30° C. and a precooled mixture of $N_\omega$-nitro-L-arginyl-L-proline ethylamide hydrochloride (0.836 g., 2.2 mmole) and triethylamine (1.43 ml., 10.2 mmole) in dimethylformamide (10 ml.) was added. The reaction mixture was stirred at −10° C for one hour and at 4° C for 48 hours. It was worked up in the usual manner and the pentapeptide derivative was purified by silica gel column chromatography using chloroform and 3% v/v methanol in chloroform as eluting solvents, yield 0.695 g. (38.5%), $R_fA$ 0.71, $R_fB$ 0.72, $R_fC$ 0.84.

Step ⑪ (R=H). Catalytic reduction with 5% w/w palladium-on-charcoal in 80% v/v aqueous acetic acid containing two equivalents of hydrogen chloride.

Step ⑫. To a vigorously stirred and cooled (−20° C.) solution of N-benzyloxycarbonyl-L-tryptophane (33.84 g., 100 mmole) and N-methyl morpholine (11.0 ml., 100 mmole) in tetrahydrofuran (200 ml.), ethyl chloroformate (9.0 ml., 95 mmole) was added. After 2 min. a precooled (−20° C.) solution of L-serine methyl ester hydrochloride (17.10 g., 110 mmole) and N-methyl morpholine (12.1 ml., 110 mmole) in dimethylformamide (150 ml.) was added and the stirring was continued at −20° C. for 30 min. and at room temperature for 3 hours. Usual work up gave an oil. Two crystallisations from ethyl acetate/petroleum ether (b.p. 60°–80° C.) gave the dipeptide derivative (30.53 g., 69.5%), m.p. 140.5°–141° C., $[\alpha]_D^{24}$ −22.13° (c, 1.4 in dimethylformamide).

Step ⑬. The preceeding ester (30.53 g., 69.5 mmole) was dissolved in methanol (1 liter) and a 62% w/v solution of hydrazine hydrate (15 ml.) was added to it. After 16 hours the hydrazine was collected, washed with methanol and ether and crystallised from hot ethanol (23.18 g., 75.8%), m.p. 178°–179° C., $[\alpha]_D^{24}$ −25.27° (c, 1 in dimethylformamide) $R_fD$ 0.65, $R_fE$ 0.20, $R_fF$ 0.43, $R_fH$ 0.50.

Steps ⑭ and ⑮. 6.02N Hydrogen chloride in dioxane (0.77 ml., 4.64 mmole) was added to a cooled (−20° C.) and stirred solution of N-benzyloxycarbonyl-L-tryptophyl-L-serine hydrazide (0.502 g., 1.16 mmole) in dimethylformamide (5 ml.) followed by t-butyl nitrite (0.14 ml., 1.22 mmole). After 30 minutes the solution was cooled to −30° C. and was neutralised by the addition of triethylamine (0.65 ml., 4.65 mmole). A precooled (−20° C.) mixture of L-tyrosylazaglycyl-L-leucyl-L-arginyl-L-proline ethylamide dihydrochloride (0.547 g., 0.77 mmole), and triethylamine (0.108 ml., 0.77 mmole) in dimethylformamide (5 ml.) was added and the stirring was continued for 1 hour at −20° C. and for 48 hours at 4° C. The reaction mixture was filtered and the filtrate was evaporated to dryness in vacuo. The crude peptide was purified by silica gel column chromatography using chloroform, 10% v/v methanol in chloroform, and a mixture of chloroform-methanol-water (11:8:2 v/v) as eluting solvents, yield 0.424 g. (52.9%), $[\alpha]_D^{25}$ −16.84° (c, 1.5 in methanol), $R_fA$ 0.61, $R_fC$ 0.36, $R_fD$ 0.67, $R_fK$ 0.90.

Step ⑱ (R=Me). As step ⑤, yield 66%, m.p. 102°–104° C., $[\alpha]_D^{24}$ −15.5° (c, 1 in methanol), $R_fD$ 0.76, $R_fE$ 0.68, $R_fF$ 0.76, $R_fH$ 0.74.

Step ⑲ (R=Me). As step ⑥.

Step ⑳ (R=Me). As step ⑦, yield 93%, m.p. 145°–146° C., $[\alpha]_D^{25}$ +8.7° (c, 1.2 L in methanol), $R_fA$ 0.88, $R_fB$ 0.88, $R_fC$ 0.83, $R_fD$ 0.80, $R_fE$ 0.59, $R_fF$ 0.78, $R_fH$ 0.73.

Step ㉑. 1N Sodium hydroxide (12 ml., 12 mmole) was added to a stirred solution of N-benzyloxycarbonyl-O-benzyl-L-tyrosylazalanyl-L-leucine methyl ester (2.41 g., 4 mmole) in methanol (36 ml.) at room temperature and the stirring was continued for 3 hours. Methanol was removed in vacuo and an aqueous solution (40 ml.) of the residue was acidified with citric acid (pH 3) and extracted with ethyl acetate. After washing the ethyl acetate extracted with water and drying (Na$_2$SO$_4$), the solvent was evaporated and the residue, in a mixture of dimethylformamidewater (3:2 v/v, 200 ml.) was applied to a column of AG 1 x-2 resin (100 ml.). The column was washed with the above solvent (50 ml.) and the tripeptide was eluted with 0.2M acetic acid in dimethylformamide-water (3:2 v/v). The tripeptide containing fractions were combined, evaporated in vacuo and the residue triturated with ether and collected, 1.22 g. (51.7%), m.p. 195° C. (decomp.), $[\alpha]_D^{24}$ −25.4° (c, 1 in dimethylformamide).

Step ㉒ (R=Me). As step ㉘, yield 43%, $[\alpha]_D^{25}$ −25.9° (c, 1 in methanol), $R_fA$ 0.72, $R_fB$ 0.76, $R_fC$ 0.85.

Step ㉓ (R=Me). As step ⑪.

Step ㉔ (R=Me). Same as step ⑮ except that the final product was also purified by gel filtration on Sephadex LH-20 in dimethylformamide after silica gel column chromatography, yield 63%, $[\alpha]_D^{25}$ −24.76° (c, 0.8 in methanol), $R_fA$ 0.58, $R_fC$ 0.42, $R_fD$ 0.65, $R_fK$ 0.95.

Step ㉕. To a stirred and cooled (0° C.) suspension of N-benzyloxycarbonyl-L-proline (24.9 g., 100 mmole), semicarbazide hydrochloride (11.2 g., 100 mmole) and triethylamine (14.5 ml., 100 mmole) in dimethylformamide (200 ml.), dicyclohexylcarbodiimide (20.6 g., 100 mmole) was added and stirring was continued for 16 hours at 4° C. Dicyclohexylurea was removed by filtration and the filtrate was evaporated to a small volume. Water (200 ml.) was added and the solution was extracted with ethyl acetate (3 × 50 ml.). The product precipitated out of the aqueous solution in about an hour. Recrystallisation from aqueous methanol gave the dipeptide amide (16.5 g., 53.9%), m.p. 189°–190° C., $[\alpha]_D^{24}$ −43.6° (c, 1.4 in dimethylformamide), $R_fD$ 0.54, $R_fF$ 0.52, $R_fH$ 0.38, $R_fK$ 0.78.

Step ㉖. Catalytic reduction over 5% w/w palladium-on-charcoal in 80% v/v aqueous dimethylformamide for six hours at room temperature in presence of two equivalents of hydrogen chloride.

Step ㉗. Ethyl chloroformate (2.83 ml., 29.5 mmole) was added to a solution of N-benzyloxycarbonyl-L-leucine (8.24 g., 31 mmole) and triethylamine (4.55 ml., 32.5 mmole) in tetrahydrofuran (100 ml.) at −10° to −15° C. The reaction mixture was stirred for 3 minutes at this temperature and was then poured into a vigorously stirred solution of N$^\omega$-nitro-L-arginine (5.79 g., 31 mmole) in 2N sodium hydroxide (15.5 ml., 31 mmole) and dimethylformamide (50 ml.) at −10° C. Stirring was continued at −10° C. for 30 minutes and then at room temperature for one hour. The solvents were removed in vacuo and the residue was distributed between ethyl acetate (50 ml.) and water (50 ml.). Aqueous phase was separated and extracted with two further portions of ethyl acetate. Combined organic phases were washed once more with water (25 ml.) and discarded. The combined aqueous phases were acidified with saturated citric acid solution and extracted with ethyl acetate (3 × 100 ml.). Ethyl acetate extracts were combined, washed with water, dried (Na$_2$SO$_4$) and evaporated to dryness. Recrystallisation of the residue from ethyl acetate/petroleum ether (b.p. 60°–80° C.) gave the dipeptide (8.98 g., 62%), m.p. 150°–165° C. (decomp.).

Step ㉘. A solution of N-benzyloxycarbony-L-leucyl-(N$^\omega$-nitro)-L-arginine (9.2 g., 20 mmole), L-prolylazaglycine amide hydrochloride (4.2 g., 20mmole), 1-hydroxybenzotriazole (5.4 g., 40 mmole) and triethylamine (3 ml., 20 mmole) in dimethylformamide (200 ml.) was cooled to 0° C. and dicyclohexylcarbodiimide (8.2 g., 40 mmole) was added to it. The reaction mixture was stirred overnight at room temperature. Dicyclohexylurea was removed by filtration and the filtrate was evaporated to dryness. Recrystallisation of the residue from methanol-ether gave the tetrapeptide derivative (12.2 g., 98.3%), m.p. 88°–90° C., $[\alpha]_D^{24}$ −30.2° (c, 1.6 in dimethylformamide), $R_fD$ 0.57, $R_fF$ 0.40, $R_fH$ 0.26, $R_fK$ 0.63.

Step ㉙. Hydrogenation over 5% w/w palladium-on-charcoal in aqueous ethanol for 16 hours in presence of two equivalents of hydrogen chloride.

Step ㉚. N-Benzyloxycarbonyl-O-benzyl-L-tyrosine-2,4,5-trichlorophenyl ester (6.484 g., 11.0 mmole) and D-alanine methyl ester hydrochloride (1.396 g., 10 mmole) were dissolved in dimethylformamide (50 ml.) and triethylamine (1.4 ml., 10.0 mmole) was added to the solution which was stirred overnight at room temperature. The reaction mixture was worked up in the usual manner and the residue was crystallised from hot ethyl acetate to yield 3.782 g., 77.2% of the protected dipeptide methyl ester, m.p. 163° C., $[\alpha]_D^{24.8}$ −12.84° (c, 1.1 dimethylformamide).

Step ㉛. N-Benzyloxycarbonyl-O-benzyl-L-tyrosyl-D-alanine methyl ester (3.435 g., 7.0 mmole) was dissolved in warm methanol (400 ml.) and the solution was treated with 62% w/v hydrazine hydrate (10 ml., 120 mmole) and the mixture was left at 25° C. overnight. The hydrazide was filtered off, washed with methanol and ether, and crystallised twice from boiling methanol, yield 3.068 g., 89.2% m.p. 217° C., $[\alpha]_D^{24}$ −20.44° (c, 1.1 in dimethylformamide) $R_fA$ 0.73, $R_fB$ 0.75, $R_fC$ 0.67, $R_fD$ 0.70, $R_fE$ 0.50, $R_fF$ 0.54, $R_fH$ 0.67, $R_fK$ 0.85, $R_fQ$ 0.25.

Steps ㉜ and ㉝. To a cooled (−20° C.) and stirred solution of N-benzyloxycarbonyl-O-benzyl-L-tyrosyl-D-alanine hydrazide (1.18 g., 2.4 mmole) a 6.02M solution of hydrogen chloride in dioxan (1.6 ml., 9.6 mmole) was added followed by t-butyl nitrite (0.29 ml., 2.52 mmole). After 15 minutes a precooled (−20° C.) solution of L-leucyl-L-arginyl-L-prolylazaglycine amide dihydrochloride chloride (1.03 g., 2.0 mmole) and triethylamine (1.62 ml., 11.6 mmole) in dimethylformamide (15 ml.) was added. The stirring was continued at 4° C. for 24 hours. Triethylamine hydrochloride was removed by filtration and the filtrate was evaporated to dryness in vacuo. The residue was loaded on a silica gel column and the column was eluted with 5% v/v methanol in chloroform, 10% v/v methanol in chloroform and a mixture of chloroform/methanol/water (11:8:2 v/v). The product containing fractions were combined, and evaporated and the peptide was chromatographed again on a silica gel column using acetronitrile/water (3:1 v/v) as eluting solvent, yield 890 mg. (46.4%), $[\alpha]_D^{25}$ −45.7° (c, 1.1 in methanol), $R_fA$ 0.54, $R_fB$ 0.69, $R_fC$ 0.41.

Step 34. As step 11.

Step 35. As step 15, yield 43%, $[\alpha]_D^{25}$ −41.4° (c, 1.3 in methanol), $R_fA$ 0.80, $R_fC$ 0.47, $R_fD$ 0.65, $R_fK$ 0.95.

Step 38. As step 3, yield 69%, m.p. 135° C., $R_fA$ 0.49, $R_fB$ 0.65, $R_fC$ 0.46, $R_fD$ 0.64, $R_fF$ 0.35, $R_fH$ 0.19, $R_fK$ 0.86.

Step 39. As step 4.

Step 40 (A=D-Phe). A solution of N-benzyloxycarbonyl-D-phenylalanine (7.41 g., 24.8 mmoles) and L-leucine methyl ester (3.62 g., 25 mmoles) in ethyl acetate (100 ml.) was cooled to 0° C. and dicyclohexylcarbodi-imide (5.15 g., 25 mmole) was added to it. The reaction mixture was stirred overnight at 4° C. The usual work up followed by recrystallisation of the residue from ethyl acetate/petroleum ether (b.p. 60°−80° C.) gave the dipeptide (9.1 g., 86%), m.p. 123°−124° C., $[\alpha]_D^{26}$-18.7° (c, 2.1 in methanol), $R_fD$ 0.76, $R_fE$ 0.65, $R_fF$ 0.74, $R_fH$ 0.73.

Step 41 (A=D—Phe). Catalytic reduction over 5% w/w palladium-on-charcoal in ethanol containing one equivalent of hydrogen chloride for five hours.

Step 42 (A=D-Phe). To a stirred solution of N-benzyloxycarbonyl-O-benzyl-L-tyrosine 2,4,5-trichlorophenyl ester (4.89 g., 8.36 mmole) and D-phenylalanyl-L-leucine methyl ester hydrochloride (2.5 g., 7.6 mmole) in dimethylformamide, triethylamine (1.1 ml., 7.6 mmole) was added and the stirring was continued overnight at room temperature. Triethylamine hydrochloride was filtered off and the filtrate was evaporated to dryness. Recrystallisation of the residue from aqueous methanol gave the tripeptide derivative, 3.6 g. (69.7%), m.p. 183°−184° C., $R_fD$ 0.82, $R_fE$ 0.69, $R_fH$ 0.78, $R_fP$ 0.71, $R_fQ$ 0.82.

Step 43 (A=D-Phe). A solution of the preceeding methyl ester (3.42 g., 5.04 mmole) and hydrazine hydrate (60 mmole) in dimethylformamide (30 ml.) was stirred at room temperature for 4 hours, concentrated to a small volume and the hydrazide was precipitated by the addition of water (500 ml.). It was collected washed with water, methanol/ether (1:4 v/v) and ether and dried. Yield 2.94 g. (85.9%), m.p. 179°−180° C., $R_fA$ 0.81, $R_fB$ 0.79, $R_fC$ 0.88, $R_fD$ 0.69, $R_fE$ 0.49, $R_fF$ 0.65, $R_fH$ 0.67, $R_fP$ 0.25, $R_fQ$ 0.57.

Steps 44 and 45 (A=D-Phe). A solution of 6.02M hydrogen chloride in dioxan (1.83 ml., 11 mmole) was added to a solution of N-benzyloxycarbonyl-O-benzyl-L-tyrosyl-D-phenylalanyl-L-leucine hydrazide (1.86 g., 2.75 mmole) in dimethylformamide (5 ml.) at −20° C. followed by t-butyl nitrite (0.33 ml., 2.89 mmole). After 2 minutes a precooled (−20° C.) solution of triethylamine (1.89 ml., 13.5 mmole) and $N^\alpha$-nitro-L-arginyl-L-prolylazaglycine amide hydrochloride (1.02 g., 2.5 mmole) in dimethylformamide (10 ml.) was added and the reaction mixture was stirred overnight at 4° C. usual work up gave the hexapeptide derivative which was further purified by silica gel (120 g.) column chromatography using 5% v/v methanol in chloroform, 10% v/v methanol in chloroform and a mixture of chloroform/methanol/water (11:8:2 v/v) as eluting solvents, yield 0.74 g. (29.3%), m.p. 137°−139° C., $R_fA$ 0.68, $R_fB$ 0.72, $R_fC$ 0.58, $R_fD$ 0.62, $R_fH$ 0.39, $R_fK$ 0.95.

Steps 46, 47 and 48. L-Pyroglutamyl-L-histidine hydrazide (10 mmole) was converted to the azide as described in general procedure (a) and was coupled with L-tryptophyl-L-serine methyl ester (11 mmole prepared by hydrogenating the N-benzyloxycarbonyl derivative over 5% w/w palladium-on-carbon in dimethylformamide) at −10° C. for 30 minutes and at 4° C. for 24 hours. Triethylamine hydrochloride was removed by filtration and the filtrate was evaporated to dryness. The crude peptide was purified by silica gel column chromatography using 10% v/v methanol in chloroform, 20% v/v methanol in chloroform and a mixture of chloroform/methanol/water (11:8:2 v/v) as eluting solvents, yield 70%, m.p. 142°−145° C. (decomp.), $R_fA$ 0.39, $R_fB$ 0.72, $R_fC$ 0.45, $R_fD$ 0.48, $R_fK$ 0.61.

Step 49. L-Pyroglutamyl-L-histidyl-L-tryptophyl-L-serine methyl ester (5.4 mmole) was dissolved in dimethylformamide (70 ml.) and was treated with hydrazine hydrate (100 mmole) for 4 hours. Dimethylformamide was removed in vacuo and the residue was triturated with ethanol, collected, washed with ethanol and ether and dried (88.2%), m.p. 184°−189° C., $R_fA$ 0.18, $R_fB$ 0.55, $R_fC$ 0.39, $R_fD$ 0.27, $R_fK$ 0.58.

Step 50 (A=D-Trp). Dicyclohexylcarbodi-imide (4.87 g., 23.6 mmole) was added to a solution of N-benzyloxycarbonyl-D-tryptophane (7.27 g., 21.5 mmole), leucine methyl ester (3.12 g., 21.5 mmole) and 1-hydroxybenzotriazole (5.8 g., 43 mmole) in dimethylformamide (50 ml.) at 0° C. The reaction mixture was stirred overnight at room temperature and was worked up in the usual manner. Recrystallisation from ethyl acetate/petroleum ether (b.p. 60°−80° C.) gave the dipeptide derivative (9.55 g.) which showed traces of impurities on t.l.c. It was purified by silica gel (300 g.) column chromatography by using chloroform and 5% v/v methanol in chloroform as eluting solvents. Yield 9.18 g. (91.7%), m.p. 151-153° C., $R_fA$ 0.84, $R_fB$ 0.80, $R_fC$ 0.86, $R_fD$ 0.78, $R_fE$ 0.61, $R_fF$ 0.68, $R_fH$ 0.73, $R_fP$ 0.55, $R_fQ$ 0.73.

Step 51 (A=D-Trp). Catalytic reduction in 80% v/v aqueous dimethylformamide over 5% w/w palladium-on-charcoal for five hours.

Step 52 (A=D-Trp). A solution of N-benzyloxycarbonyl-O-benzyl-L-tyrosine-2,4,5-trichlorophenyl ester (11.69 g., 20 mmole), D-tryptophyl-L-leucine methyl ester (6.28 g., 19 mmole) in dimethylformamide (100 ml.) was stirred at room temperature for 60 hours. The reaction mixture was worked up in the usual manner and the residue was crystallized from ethyl acetate/petroleum ether (b.p. 60-80° C.) to give the tripeptide derivative, 8.52 g. (62.5%), m.p. 165-166° C., $R_fA$ 0.78, $R_fB$ 0.73, $R_fC$ 0.84, $R_fD$ 0.80, $R_fE$ 0.62, $R_fF$ 0.70, $R_fH$ 0.76, $R_fP$ 0.58, $R_fQ$ 0.68.

Step 53 (A=D-Trp). A solution of N-benzyloxycarbonyl-O-benzyl-L-tyrosyl-D-tryptophyl-L-leucine methyl ester (7.26 g., 10.1 mmole) in a mixture of methanol (200 ml.) and dimethylformamide (50 ml.) was treated with hydrazine hydrate (100 mmole) at room temperature. After 24 hours the solution was concentrated (~30 ml.) and water (500 ml.) was added. The tripeptide hydrazide was collected, washed with water, methanol/ether (1:4 v/v) and ether and dried, 6.86 g. (94.6%), m.p. 200°-202° C., $R_fA$ 0.90, $R_fB$ 0.95, $R_fC$ 0.90, $R_fD$ 0.7, $R_fQ$ 0.59.

Steps 54 and 55 (A=D-Trp) A stirred and cooled (−20° C.) solution of N-benzyloxycarbonyl-O-benzyl-L-tyrosyl-D-tryptophyl-L-leucine hydrazide (1.97 g., 2.75 mmole) in dimethylformamide (10 ml.) was treated with a 6.02M solution of hydrogen chloride in dioxane (1.83 ml., 11 mmole) followed by t-butyl nitrite (0.33 ml., 2.89 mmole). After 2 minutes a precooled (−20° C.) solution of $N^\omega$-nitro-L-arginyl-L-prolylazaglycine amide hydrochloride (1.02 g., 2.5 mmole) and triethylamine (1.89 ml., 13.5 mmole) in dimethylformamide (10 ml.) was added and the reaction mixture was stirred overnight at 4° C. It was worked up in the usual manner and the residue (1.27 g.) was applied to a silica gel (230 g.) column and the column was eluted with chloroform and 5% v/v methanol in chloroform. Yield 0.91 g. (34.4%), m.p. 139°-140° C. (decomp.), $R_fA$ 0.67, $R_fB$ 0.72, $R_fC$ 0.58, $R_fD$ 0.62, $R_fH$ 0.34, $R_fK$ 0.95.

Step 56 (A=D-Tyr(Me)). A solution of Z-D-Tyr(Me)-OH (3.17 g., 9.64 mmole), Leu-OMe.HCl (1.92 g., 10.6 mmole), 1-hydroxybenzotriazole (2.6 g., 19.2 mmole) and triethylamine (1.6 ml., 11 mmole) in dimethylformamide (30 ml.) was cooled to 0° C. and N,N'-dicyclohexylcarbodi-imide (2.29 g., 11.1 mmole) was added to it. The reaction mixture was stirred overnight at 4° C. and was then worked up in the usual manner. Recrystallisation from hot cyclohexane gave the protected dipeptide derivative. Yield 1.41 g. (95.2%), $R_fD$ 0.83, $R_fE$ 0.69, $R_fP$ 0.72, $R_fQ$ 0.76.

Step 57 (A=D-Tyr(Me)). Catalytic reduction over 5% w/w palladium-on-charcoal in methanol/dimethylformamide/water (8:1:1) containing 1.2 equivalents of hydrogen chloride for three hours.

Step 58 (A=D-Tyr(Me)). A solution of Z-Tyr(Bzl)-OCp (8.2 mmole), D-Tyr(Me)-Leu-OMe.HCl (8.2 mmole), and triethylamine (8.2 mmole) in dimethylformamide (60 ml.) was stirred overnight at room temperature and the reaction mixture was then worked up in the usual manner. The product was filtered with ether, washed with ether and dried. Yield 81.2%), m.p. 191°-192° C., $R_fD$ 0.85, $R_fE$ 0.73, $R_fF$ 0.72, $R_fQ$ 0.78.

Step 59 (A=D-Tyr(Me)). Hydrazine hydrate (12.9 mmole) was added to a solution of Z-Tyr(Bzl)-D-Tyr(Me)-Leu-OMe (4.59 g., 6.4 mmole) in dimethylformamide (25 ml.) and methanol (50 ml.) and the reaction mixture was left overnight at room temperature. Methanol was removed in vacuo and the product was precipitated with water, collected, washed with water and dried, m.p. 212-213° C., $R_fE$ 0.49, $R_fF$ 0.66, $R_fH$ 0.69, $R_fQ$ 0.70.

Steps 60 and 61 (A=D-Tyr(Me)). The hydrazide from Step 59 (3.54., 5.0 mmole) was dissolved in DMF (10 ml).) and the stirred solution was cooled to −20° C. 5.92M HCl in dioxane (3.38 ml., 20 mmole) was added followed by t-butyl nitrite (0.6 ml., 5.25 mmole). After 2 minutes, a precooled solution of H-Arg(NO₂)-Pro-Azgly-NH₂.HCl (2.04 g., 5 mmole) and triethylamine (3.55 ml., 25 mmole) in DMF (10 ml.) was added and the stirring was continued overnight at 4° C. The reaction mixture was worked up in the usual manner and the crude product was purified by silica gel column chromatography using chloroform, 5% v/v methanol in chloroform and 10% v/v methanol in chloroform as eluting solvents. Yield 3.72 g. (70.9%), $R_fA$ 0.64, $R_fB$ 0.72, $R_fC$ 0.55, $R_fD$ 0.66, $R_fF$ 0.40, $R_fH$ 0.52.

Step 62 (A=D-Ser(Bu$^t$)). As Step 56. The product was crystallised from aqueous methanol. Yield 90.4%, m.p. 107°-108° C., $R_fD$ 0.80, $R_fE$ 0.68, $R_fF$ 0.73, $R_fH$ 0.72, $R_fP$ 0.72, $R_fQ$ 0.74.

Step 63 (A=D-Ser(Bu$^t$)). Catalytic reduction over 5% w/w palladium-on-charcoal in DMF-water (8:2) for five hours.

Step 64 (A=D-Ser(Bu$^t$)). A solution of Z-Tyr(Bzl)-OCp (19.17 g., 32.7 mmole) and H-Ser(Bu$^t$)-Leu-OMe (32.7 mmole) in DMF (100 ml.) was left at room temperature for 72 hours. Usual work up gave a solid which was collected, washed with ether and dried. Yield 17.6 g. (79.4%), m.p. 135°-137° C. $R_fD$ 0.80, $R_fH$ 0.77, $R_fQ$ 0.81.

Step 65 (A=D-Ser(Bu$^t$)). As step 59. Recrystallised from aqueous methanol. Yield 56.2%, m.p. 134°-136° C., $R_fD$ 0.66, $R_fH$ 0.64, $R_fQ$ 0.64.

Steps 66 and 67 (A=D-Ser(Bu$^t$)). As steps 60 and 61. The product was purified by silica gel column chromatography using chloroform and 5% v/v methanol in chloroform as eluting solvents Yield 38.5%, m.p. 142°-145° C., $R_fA$ 0.64, $R_fB$ 0.71, $R_fC$ 0.55, $R_fD$ 0.65, $R_fF$ 0.46, $R_fH$ 0.43, $R_fQ$ 0.16.

Step 68 (A=D-Tyr(Me)). Dicyclohexylcarbodi-imide (5.13 g., 24.9 mmole) was added to a cooled (0° C.) and stirred solution of Z-D-Tyr(Me)-OH (22.6 mmole), H-MeLeu-OMe.HBr (5.98 g., 24.9 mmole), triethylamine (3.5 ml., 24.9 mmole), and 1-hydroxybenzotriazole (6.12 g., 45.2 mmole) in DMF (50 ml.) and the stirring was continued overnight at 4° C. The reaction mixture was worked up in the usual manner and the product was purified by silica gel column chromotography using chloroform as solvent. Yield 55.2%, oil, $R_fD$ 0.83, $R_fE$ 0.78, $R_fH$ 0.79, $R_fP$ 0.80, $R_fQ$ 0.79.

Step 69 (A= D-Tyr(Me)). Catalytic reduction over 5% w/w palladium-on-charcoal in methanol/water (8:2 v/v) containing an equivalent of hydrogen chloride for six hours.

Step 70 (A=D-Tyr(Me)). As step 58. The product was purified by silica gel column chromatography using ether as solvent.

Step 71 (A=D-Tyr(Me)). A solution of Z-Tyr(Bzl)-D-Tyr(Me)-MeLeu-OMe (4.85 g., 6.69 mmole) and hydrazine hydrate (120.7 mmole) in methanol (150 ml.) was left overnight at room temperature. The hydrazide was precipitated by the addition of water, collected, and crystallised from methanol/water. Yield 91.1%, m.p. 129°-131° C., $R_fD$ 0.79, $R_fE$ 0.60, $R_fF$ 0.68, $R_fH$ 0.73, $R_fQ$ 0.77.

Steps 72 and 73 (A=D-Tyr(Me). As steps 60 and 61. Recrystallised from methanol/ether, yield 23.8%, m.p. 152°-154° C., $R_fA$ 0.67, $R_fB$ 0.68, $R_fC$ 0.58, $R_fD$ 0.59, $R_fH$ 0.50, $R_fK$ 0.94, $R_fQ$ 0.35.

Step 74 Ethyl chloroformate (1.8 ml., 18 mmole) was added to a cooled (−15° C.) and stirred solution of Z-Phe-OH (5.99 g., 20 mmole) and N-methylmorpholine (2.2 ml., 20 mmole) in DMF (60 ml.). After 2 minutes a precooled (−15° C.) solution of H-MeLeu-OMe.HBr (4.8 g., 20 mmole) and triethylamine (2.8 ml., 20 mmole) in DMF (20 ml.) was added and the reaction mixture was stirred for 30 minutes at 0° C. and overnight at room temperature. It was worked up in the usual manner. Yield 7.54. (90%), oil.

Step 75 Catalytic reduction over 5% w/w palladium-on-charcoal in methanol containing an equivalent of hydrogen chloride for three hours.

Step 76 Prepared by coupling Z-Tyr(Bu$^t$)-OH (16.02 g., 43.2 mmole) and H-D-Phe-MeLeu-OMe.HCl (13.15 g., 40.0 mmole) as in Step 74. The product was purified by silica gel column chromatograph using chloroform and 5% v/v methanol in chloroform as solvent. Yield 60%, oil, R$_f$G 0.48, R$_f$P 0.71, R$_f$Q 0.73.

Step 77 A solution of Z-Tyr(Bu$^t$)-D-Phe-MeLeu-OMe (6.52 g., 9.76 mmole) and hyrazine hydrate (97.6 mmole) in methanol (50 ml.) was left overnight at room temperature. Methanol was removed in vacuo and the hydrazide was crystallised from methanol/ether, washed with methanol/water (1:1 v/v) and ether and dried. Yield 5.2 g. (80%), m.p. 135° C., R$_f$D 0.75, R$_f$E 0.69, R$_f$F 0.66, R$_f$H 0.79, R$_f$Q 0.73.

Steps 78 and 79 As Steps 60 and 61. During the work up procedure the product precipitated out of ethyl acetate. It was filtered off, washed with ethyl acetate and ether and dried. Yield 58.5%, m.p. 145°–148° C., R$_f$D 0.72, R$_f$F 0.40, R$_f$H 0.53, R$_f$Q 0.18.

What we claim is:

1. A polypeptide of the formula:

Glu-His-Trp-Ser-Tyr-A-B-Arg-Pro-E-F in which A is selected from the group consisting of D-Tyr(Me), D-Ser(Bu$^t$) and D-Phe, B is selected from the group consisting of Leu or MeLeu, E is Azgly and F is an amino radical, and the pharmaceutically- and veterinarily-acceptable acid-addition salts thereof.

2. A polypeptide as claimed in claim 1 which is

Glu-His-Trp-Ser-Tyr-D-Phe-Leu-Arg-Pro-Azgly-NH$_2$.

3. A polypeptide as claimed in claim 1 which is

Glu-His-Trp-Ser-Tyr-D-Tyr(Me)-Leu-Arg-Pro-Azgly-NH$_2$.

4. A polypeptide as claimed in claim 1 which is

Glu-His-Trp-Ser-Tyr-D-Ser(Bu$^t$)-Leu-Arg-Pro-Azgly-NH$_2$.

5. A pharmaceutical or veterinary composition comprising as active ingredient an effective amount of a polypeptide as claimed in claim 1 in association with a major amount of a nontoxic pharmaceutically- or veterinarily-acceptable diluent or carrier.

6. A method of controlling and/or improving reproduction in warm-blooded animals which comprises administration of an effective amount of a polypeptide as claimed in claim 1.

* * * * *

UNITED STATES PATENT AND TRADEMARK OFFICE

CERTIFICATE EXTENDING PATENT TERM
UNDER 35 U.S.C. 156

Patent No.      : 4,100,274

Dated           : July 11, 1978

Inventor(s)     : Anand Swaroop Dutta et al

Patent Owner    : Imperial Chemical Industries PLC

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

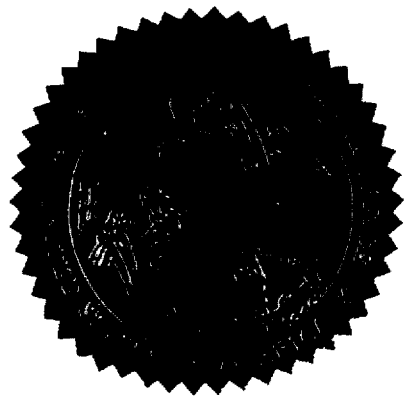

I have caused the seal of the Patent and Trademark Office to be affixed this 7th day of December 1990.

Harry F. Manbeck, Jr.
Assistant Secretary and Commissioner
  of Patents and Trademarks